(12) United States Patent  
Connor

(10) Patent No.: US 8,641,723 B2  
(45) Date of Patent: Feb. 4, 2014

(54) SKELETAL ADJUSTMENT DEVICE

(75) Inventor: Robert A. Connor, Minneapolis, MN (US)

(73) Assignee: Orthonex LLC, Forest Lake, MN (US)

( * ) Notice: Subject to any disclaimer, the term of this patent is extended or adjusted under 35 U.S.C. 154(b) by 88 days.

(21) Appl. No.: 13/134,069

(22) Filed: May 28, 2011

(65) Prior Publication Data

US 2011/0301645 A1    Dec. 8, 2011

Related U.S. Application Data

(60) Provisional application No. 61/396,921, filed on Jun. 3, 2010.

(51) Int. Cl.  
*A61B 17/58* (2006.01)

(52) U.S. Cl.  
USPC .............................................. 606/105; 606/57

(58) Field of Classification Search  
USPC ............... 606/57, 63, 105, 251, 252, 258, 58, 606/282, 90  
See application file for complete search history.

(56) References Cited

U.S. PATENT DOCUMENTS

| | | | |
|---|---|---|---|
| 3,976,060 A * | 8/1976 | Hildebrandt et al. ......... | 606/241 |
| 5,092,866 A | 3/1992 | Breard et al. | |
| 5,350,379 A | 9/1994 | Spievack | |
| 5,466,261 A * | 11/1995 | Richelsoph ................ | 623/23.47 |
| 5,501,684 A | 3/1996 | Schlapfer et al. | |
| 5,505,733 A | 4/1996 | Justin et al. | |
| 5,575,790 A | 11/1996 | Chen et al. | |
| 5,626,579 A | 5/1997 | Muschler et al. | |
| 5,672,175 A | 9/1997 | Martin | |
| 5,704,939 A | 1/1998 | Justin | |
| 5,720,746 A | 2/1998 | Soubeiran | |
| 5,961,553 A | 10/1999 | Coty et al. | |
| 6,033,412 A | 3/2000 | Losken et al. | |
| 6,106,525 A | 8/2000 | Sachse | |
| 6,245,075 B1 | 6/2001 | Betz et al. | |
| 6,336,929 B1 | 1/2002 | Justin | |
| 6,375,682 B1 | 4/2002 | Fleischmann et al. | |
| 6,417,750 B1 | 7/2002 | Sohn | |
| 6,565,576 B1 * | 5/2003 | Stauch et al. ................. | 606/105 |
| 6,673,079 B1 | 1/2004 | Kane | |
| 6,682,533 B1 | 1/2004 | Dinsdale et al. | |
| 6,716,216 B1 | 4/2004 | Boucher et al. | |
| 6,796,984 B2 | 9/2004 | Soubeiran | |
| 6,835,207 B2 | 12/2004 | Zacouto et al. | |
| 6,849,076 B2 | 2/2005 | Blunn et al. | |
| 6,918,910 B2 | 7/2005 | Smith et al. | |
| 7,066,957 B2 | 6/2006 | Graf | |
| 7,135,022 B2 | 11/2006 | Kosashvili et al. | |
| 7,291,150 B2 | 11/2007 | Graf | |

(Continued)

*Primary Examiner* — Jan Christopher Merene

(57) ABSTRACT

This invention is an implantable device that enables non-invasive post-operative adjustment of the motion dynamics between two members of the human skeletal system. It may be used for dynamic stabilization of the spine. This device includes: a flowable substance; a reservoir implanted into the human body that contains this flowable substance wherein movement of moving portions of this reservoir causes the flowable substance to flow; and an energy-transducing mechanism wherein this mechanism transduces energy from a flow of the flowable substance into changes in the motion dynamics between the two members of the human skeletal system. This device may be used for: (1) non-invasive post-implantation customization of the device to reduce back pain for a particular patient; (2) non-invasive gradual adjustment of the device to correct spinal deformities; and (3) real-time adjustment to optimize spinal motion dynamics as the patent engages in different activities.

6 Claims, 14 Drawing Sheets

(56) References Cited

U.S. PATENT DOCUMENTS

| | | | |
|---|---|---|---|
| 7,335,200 B2 | 2/2008 | Carli | |
| 7,361,196 B2 | 4/2008 | Fallin et al. | |
| 7,481,841 B2 | 1/2009 | Hazebrouck et al. | |
| 7,559,951 B2 | 7/2009 | DiSilvestro et al. | |
| 7,604,654 B2 | 10/2009 | Fallin et al. | |
| 7,611,526 B2 | 11/2009 | Carl et al. | |
| 7,625,393 B2 | 12/2009 | Fallin et al. | |
| 7,658,753 B2 | 2/2010 | Carl et al. | |
| 7,662,173 B2 | 2/2010 | Cragg et al. | |
| 7,708,737 B2 | 5/2010 | Kraft et al. | |
| 7,708,765 B2 | 5/2010 | Carl et al. | |
| 7,708,779 B2 | 5/2010 | Edie et al. | |
| 7,722,675 B2 | 5/2010 | Ralph et al. | |
| 7,736,305 B2 | 6/2010 | DiPoto | |
| 7,763,053 B2 | 7/2010 | Gordon | |
| 7,766,941 B2 | 8/2010 | Paul | |
| 8,043,299 B2 * | 10/2011 | Conway | 606/105 |
| 8,211,149 B2 * | 7/2012 | Justis | 606/258 |
| 2002/0151978 A1 | 10/2002 | Zacouto et al. | |
| 2004/0152972 A1 | 8/2004 | Hunter | |
| 2005/0055025 A1 | 3/2005 | Zacouto et al. | |
| 2005/0234555 A1 | 10/2005 | Sutton et al. | |
| 2006/0004447 A1 | 1/2006 | Mastrorio et al. | |
| 2006/0036246 A1 | 2/2006 | Carl et al. | |
| 2006/0036256 A1 | 2/2006 | Carl et al. | |
| 2006/0036259 A1 | 2/2006 | Carl et al. | |
| 2006/0036324 A1 | 2/2006 | Sachs et al. | |
| 2007/0173855 A1 | 7/2007 | Winn et al. | |
| 2007/0232958 A1 | 10/2007 | Donofrio et al. | |
| 2007/0233065 A1 | 10/2007 | Donofrio et al. | |
| 2007/0233098 A1 | 10/2007 | Mastrorio et al. | |
| 2007/0233254 A1 | 10/2007 | Grotz et al. | |
| 2007/0239161 A1 | 10/2007 | Giger et al. | |
| 2007/0255088 A1 | 11/2007 | Jacobson et al. | |
| 2007/0270803 A1 | 11/2007 | Giger et al. | |
| 2007/0276369 A1 | 11/2007 | Allard et al. | |
| 2008/0021466 A1 | 1/2008 | Shadduck et al. | |
| 2008/0154307 A1 | 6/2008 | Colleran et al. | |
| 2008/0161933 A1 | 7/2008 | Grotz et al. | |
| 2009/0012565 A1 | 1/2009 | Sachs et al. | |
| 2009/0076597 A1 | 3/2009 | Dahlgren et al. | |
| 2009/0093820 A1 | 4/2009 | Trieu et al. | |
| 2009/0112207 A1 | 4/2009 | Walker et al. | |
| 2009/0112262 A1 | 4/2009 | Pool et al. | |
| 2009/0112263 A1 | 4/2009 | Pool et al. | |
| 2009/0234388 A1 | 9/2009 | Patterson et al. | |
| 2009/0234456 A1 | 9/2009 | Nycz | |
| 2009/0281542 A1 * | 11/2009 | Justis | 606/60 |
| 2010/0049204 A1 | 2/2010 | Soubeiran | |
| 2010/0063548 A1 | 3/2010 | Wang | |
| 2010/0070033 A1 | 3/2010 | Doty | |
| 2010/0094302 A1 | 4/2010 | Pool | |
| 2010/0094303 A1 | 4/2010 | Chang et al. | |
| 2010/0094304 A1 | 4/2010 | Pool | |
| 2010/0094305 A1 | 4/2010 | Chang | |
| 2010/0094306 A1 | 4/2010 | Chang | |
| 2010/0100133 A1 | 4/2010 | Carl et al. | |
| 2010/0114103 A1 | 5/2010 | Harrison et al. | |
| 2010/0191288 A1 | 7/2010 | Carl et al. | |
| 2010/0198261 A1 | 8/2010 | Trieu et al. | |
| 2010/0262160 A1 | 10/2010 | Boyden et al. | |
| 2010/0262239 A1 | 10/2010 | Boyden et al. | |
| 2010/0262247 A1 | 10/2010 | Arnin | |

* cited by examiner

SKELETAL ADJUSTMENT DEVICE

CROSS-REFERENCE TO RELATED APPLICATIONS

This patent application claims the priority benefits of: U.S. Provisional Patent Application No. 61/396,921 entitled "Skeletal Adjustment Device" filed on Jun. 3, 2010 by Robert A. Connor.

FEDERALLY SPONSORED RESEARCH

Not Applicable

SEQUENCE LISTING OR PROGRAM

Not Applicable

BACKGROUND

Field of Invention

This invention relates to implantable medical devices that adjust the motion dynamics between members of the skeletal system.

INTRODUCTION

There is an unmet clinical need for an implantable medical device that can enable non-invasive, post-operative adjustment of spinal motion dynamics. Spinal motion dynamics include: direction of spinal motion (flexion, extension, lateral bending, and torsion); range of spinal motion (flexion, extension, lateral bending, and torsion); and resistance of spinal motion (flexion, extension, lateral bending, and torsion) to external force. There are three main clinical applications of such a device. The first clinical application for such a device is non-invasive adjustment and customization of the device to optimize spinal motion dynamics to reduce back pain for a particular patient, generally shortly after implantation. Such adjustment and customization is useful because some of the specific interactions between a device and the patient's spine are not fully known until after the device is actually implanted. The second application is long-term, gradual, non-invasive adjustment of the device to gradually correct spinal deformities (such as scoliosis) or injuries. The third application is ongoing, cyclical, non-invasive adjustment of the device over time to optimize spinal motion dynamics as the patent engages in different activities (eg. sports vs. sleeping) during the day. Such intra-day real-time adjustment of motion dynamics is analogous to the way in which modern pacemakers adjust heart pacing throughout the day to better support the different activities in which the patient engages.

One of the main challenges in creating an implantable device to address this unmet clinical need for non-invasive, post-operative adjustment of spinal motion dynamics is how to power the device. The prior art includes different approaches and attempts to power such devices, but these approaches all have significant limitations. A device may be powered by an implantable battery, as is a pacemaker, but the relatively significant energy demands of adjusting skeletal members are likely to require the inconvenience of either a relatively bulky battery or very frequent battery recharging. A device may be powered by induction of an internal drive member by an external electromagnetic field, but this approach can result in harmful outcomes from exposure to strong magnetic fields such as those used in Magnetic Resonance Imaging (MRI). This approach also requires use of specialized equipment. A device may be powered by injection of fluid from an external source such as a syringe, but this approach penetrates the skin (increasing the risk of infection) and is not well-suited for reversible or cyclical adjustments. A device may be powered by the natural movement of internal body members, but this is not a dependable source of power for spinal applications due to the relatively low degree of spinal movement and due to inter-patient variability in this movement. This application discloses a novel invention that overcomes these limitations of the prior art. This invention fulfills an unmet clinical need by enabling non-invasive, post-operative adjustment of spinal motion dynamics.

Unmet Clinical Need and Limitations of the Prior Art

Chronic lower back pain is a very common, significant, and costly health problem in the United States and the entire world. It is estimated that more than ten million people in the U.S. alone suffer from chronic back pain at any given time, that the annual prevalence of lower back pain is in the range of 15-45% of the population, and that thoracic and lumbar spinal disorders affect nearly three-quarters of the U.S. population some time during their lives. Chronic back pain can be debilitating, interfering with one's ability to work and enjoy recreational activities. It is the most common activity-limiting condition affecting people under the age of 45.

The leading cause of chronic lower back pain is degeneration of the semi-flexible discs between the spinal vertebrae. There are non-surgical approaches to addressing chronic back pain, but sometimes they are inadequate and more invasive methods are required. Historically, a common surgical method has been to fuse selected spinal vertebrae together in an effort to eliminate disc movement and stop the pain. More than 150,000 lumbar fusions are done each year to immobilize selected vertebrae. However, there are limitations associated with fusing vertebrae. Fusion-related limitations include: undesirable restriction of natural spine movement (restrictions on spinal flexion, extension, lateral bending, and torsion) in fused segments; greater stress and degeneration affecting spinal segments adjacent to fused segments (a phenomenon called "transition syndrome"); bone loss in the immobilized segments; failure to stop the pain in approximately 20-25% of fusion cases; irreversibility of the procedure; and the invasiveness, health risks, and relatively long recovery period associated with the surgery.

Due to the limitations associated with the complete immobilization of selected vertebrae in fusion, there has been an increasing trend toward alternative methods of addressing back pain that preserve some spinal mobility. "Dynamic stabilization" is the term that was created for methods that seek to maintain desirable spinal movement, but limit undesirable spinal movement. Dynamic stabilization is an effort to: relieve the load and correct improper vertebral movement in areas where pain is caused by compression and improper vertebral movement; maintain proper rigidity, stabilization, and vertical support of the spinal column; avoid abnormal range of motion; and ensure the long-term durability of the spinal structure, including any implants; allow normal biomechanical direction and range of motion including flexion (bending forward/anteriorly), extension (bending backward/posteriorly), lateral bending (right and left side bending), torsion (axial rotational movement), and limited longitudinal elongation or compression (so-called "shock absorber" functionality). In addition to the mobility and comfort advantages for patients, allowing normal motion can also help to avoid loss of bone density for diseased segments and more evenly distribute load across different portions of the spinal column to avoid creating stress-induced problems elsewhere. Allowing desirable spinal movement is particularly important for young patients.

Progress has been made toward developing devices and methods for dynamic stabilization of the spine, but current treatment options have limitations. Some methods and devices may be prone to mechanical or material failure, or inconsistent performance over time, due to the repeated flexing of materials or components. Some methods and devices are not adjustable or customizable to meet the specific needs and features of different patients. For example, they may not be non-invasively adjustable after implantation to refine therapy or to accommodate patient growth. Accordingly, there is still a need for new approaches to dynamic stabilization that address these limitations and provide better treatment options for the millions of people who suffer from chronic back pain. That is the motivation for this application.

U.S. Patent Application No. 20090012565 (Sachs et al., "Medical Device and Method to Correct Deformity") appears to disclose a spinal distracting device with a motor that is powered by an implanted battery. U.S. Pat. Nos. 7,481,841 (Hazebrouck et al., "Adjustable Orthopaedic Prosthesis and Associated Method"), 7,135,022 (Kosashvili et al., "Magnetically-Actuable Intramedullary Device"), and 6,849,076 (Blunn et al., "Surgical Distraction Device") appear to disclose skeletal distraction devices that are powered by application of an electromagnetic field from an external source. U.S. Pat. No. 6,245,075 (Betz et al., "Distraction Device for Moving Apart Two Bone Sections") appears to disclose a bone distracting device with a motor powered either by a battery or by application of an electromagnetic field from an external source. Due to the power requirements of physically moving skeletal members, prior art that relies on an implanted battery for power is likely to require an undesirably-large battery, frequent recharging, or both. Prior art that relies on electromagnetic induction may cause tissue damage when the implanted hardware is exposed to strong magnetic fields such as the fields used in increasingly-prevalent imaging modalities such as Magnetic Resonance Imaging (MRI). Exposure of such implanted hardware to strong magnetic fields may tear or burn contiguous body tissue.

U.S. Pat. Nos. 6,918,910 (Smith at al., "Implantable Distraction Device"), 6,673,079 (Kane, "Device for Lengthening and Reshaping Bone by Distraction Osteogenesis"), and 6,106,525 (Sachse, "Fully Implantable Bone Expansion Device"), and U.S. Patent Application No 20070276369 (Allard et al., "In Vivo-Customizable Implant") appear to disclose skeletal distraction devices that are powered by injection of a fluid through the skin from an external source, such as a syringe. Repeated penetration of the skin increases the risk of infection. Also, such injections are inconvenient and it is unclear whether external injection approaches allow reversible or cyclical actions that would require fluid extraction.

U.S. Pat. Nos. 6,106,525 (Sachse, "Fully Implantable Bone Expansion Device") and 7,708,737 (Kraft et al., "Intramedullar Distraction Device with User Actuated Distraction") appear to disclose rigid bone-elongation devices that are powered by pushing an implanted button or hydraulic disk. Although potentially useful for bone elongation applications, these rigid devices do not allow post-surgical adjustment of spinal motion dynamics such as spinal flexion, spinal extension, spinal lateral bending, and spinal torsion.

To summarize, although there has been progress toward dynamic stabilization of the spine, the prior art does not yet disclose an implantable medical device that enables non-invasive, post-operative adjustment of spinal motion dynamics. Such adjustment is an unmet clinical need for applications including: non-invasive adjustment of the device to optimize spinal motion dynamics shortly after implantation; long-term, gradual, non-invasive adjustment of the device over time to gradually correct spinal deformities or injuries; and ongoing, cyclical, non-invasive adjustment of the device over time to optimize spinal motion dynamics in real time as the patent engages in different activities. The novel invention disclosed herein addresses these limitations of the prior art and can address these unmet clinical needs.

SUMMARY AND ADVANTAGES OF THIS INVENTION

This invention is an implantable medical device that enables non-invasive post-operative adjustment of the motion dynamics between a first member of the human skeletal system and a second member of the human skeletal system. In an example, this device may be used for dynamic stabilization of the spine. Spinal motion dynamics include: direction of spinal motion (flexion, extension, lateral bending, and torsion); range of spinal motion (flexion, extension, lateral bending, and torsion); and resistance of spinal motion (flexion, extension, lateral bending, and torsion) to external force.

This device includes: a flowable substance; a reservoir implanted into the human body that contains this flowable substance wherein movement of moving portions of this reservoir causes the flowable substance to flow; and an energy-transducing mechanism wherein this mechanism transduces energy from a flow of the flowable substance into changes in the motion dynamics between the first member of the human skeletal system and the second member of the human skeletal system. This device may optionally be adjusted by a wireless remote control unit.

This device may be used in at least three clinical applications. First, this device may be used for non-invasive adjustment and customization of the device to optimize spinal motion dynamics to reduce back pain for a particular patient. Secondly, this device may be used for gradual, non-invasive adjustment of the device to gradually correct spinal deformities such as scoliosis. Thirdly, this device may be used for real-time adjustment of the device over time to optimize spinal motion dynamics as the patent engages in different activities (eg. sports vs. sleeping) during the day.

This invention addresses limitations of the prior art in this area. It avoids the problems associated with implanted batteries and implanted electromagnetic induction hardware in the prior art. For example, it avoids tissue damage from exposure of electromagnetic implants to strong magnetic fields, such as those used in Magnetic Resonance Imaging. It also avoids the need for repeated access to specialized recharging equipment. This invention also avoids the infection risk and inconvenience of repeated injections through the skin. Further, this invention enables non-invasive adjustment of motion dynamics that is not possible with bone fixation and lengthening devices in the prior art.

BRIEF DESCRIPTION OF DRAWINGS

FIGS. 1 and 2 show an example that changes the motion dynamics between two members of the human skeletal system using parallel rods between the two members. FIG. 1 shows this example wherein the configuration of the rods allows less relative movement of the two members. FIG. 2 shows this example wherein the configuration of the rods allows more relative movement of the two members.

FIGS. 3 and 4 show an example that changes the motion dynamics between two members of the human skeletal system using a longitudinal flexible member between the two members. FIG. 3 shows this example wherein the length and/or tension of the longitudinal member allows more relative movement of the two members. FIG. 4 shows this same example wherein the length and/or tension of the longitudinal member allows less relative movement of the two members.

FIGS. 5 and 6 show an example that changes the motion dynamics between two members of the human skeletal system using a motion-dampening member between the two members. FIG. 5 shows this example wherein the motion-dampening member allows more relative movement of the two members. FIG. 6 shows this same example wherein the motion-dampening member allows less relative movement of the two members.

FIGS. 7 and 8 show an example that draws two members of the human skeletal system closer together using a pair of thread-engaged members. FIG. 7 shows this example wherein the two members are farther apart. FIG. 8 shows this same example wherein the two members are closer together.

FIGS. 9 and 10 show an example that draws two members of the human skeletal system closer together using a pair of notch-engaged members. FIG. 9 shows this example wherein the two members are farther apart. FIG. 10 shows this same example wherein the two members are closer together.

FIGS. 11 and 12 show an example that increases the distance between two members of the human skeletal system using concentrically-overlapping members ("telescoping") filled with a flowable substance. FIG. 11 shows this example wherein the two members are closer together. FIG. 12 shows this same example wherein the two members are farther apart.

FIGS. 13 and 14 show an example of this invention wherein energy from the flow of a flowable substance drives an electric generator that provides electricity to power an electric motor that is used to change the distance between two members of the human skeletal system. FIG. 13 shows this example when the two members are farther apart. FIG. 14 shows this same example wherein the two members are closer together.

DETAILED DESCRIPTION OF THE FIGURES

The following figures show several examples of how this invention may be embodied. However, these are only some of the possible embodiments. These figures do not limit the full generalizability of the claims.

Figure 1:
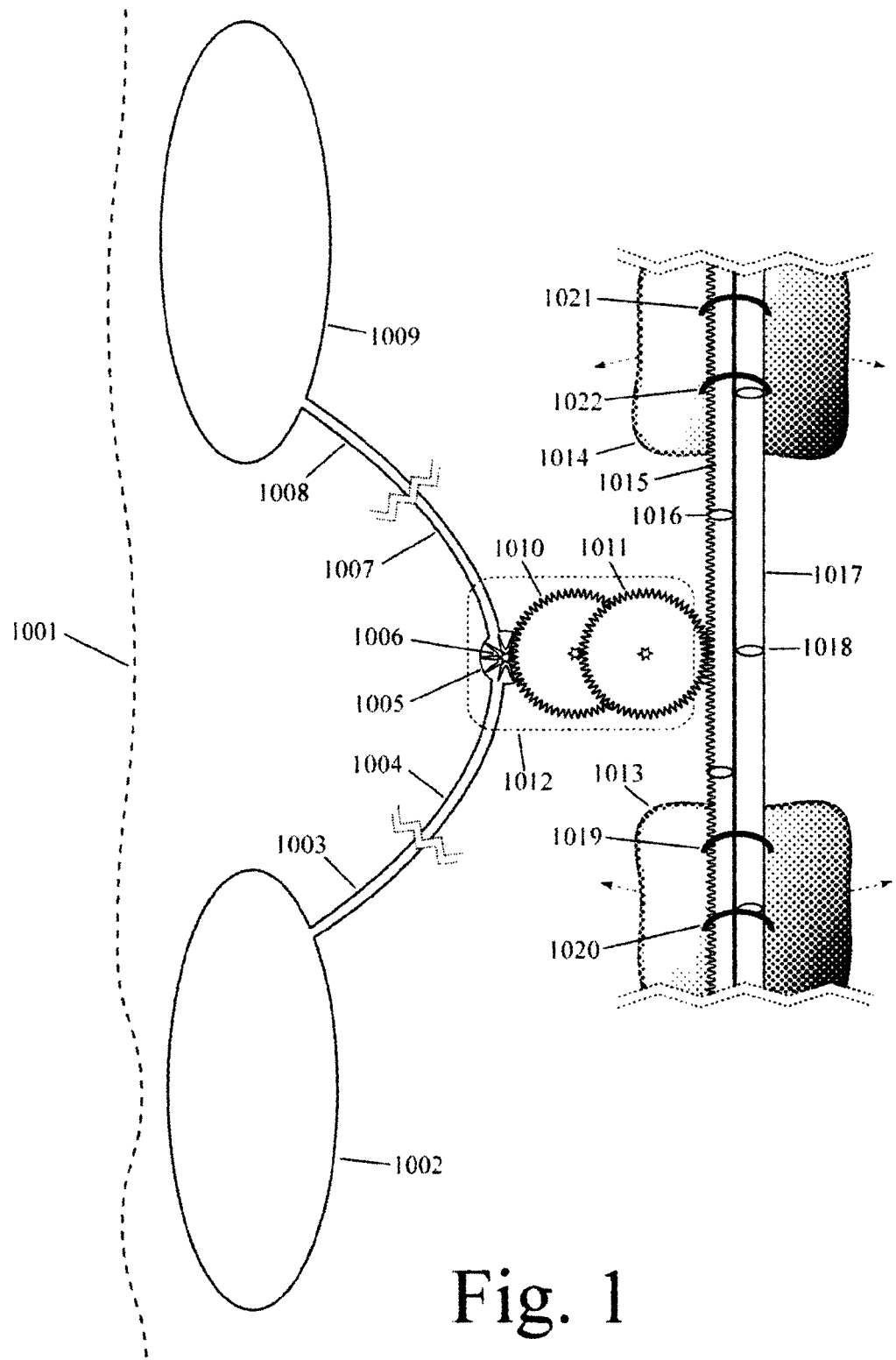
FIGS. 1 through 14 show examples of how this invention may be embodied.
Figure 2:
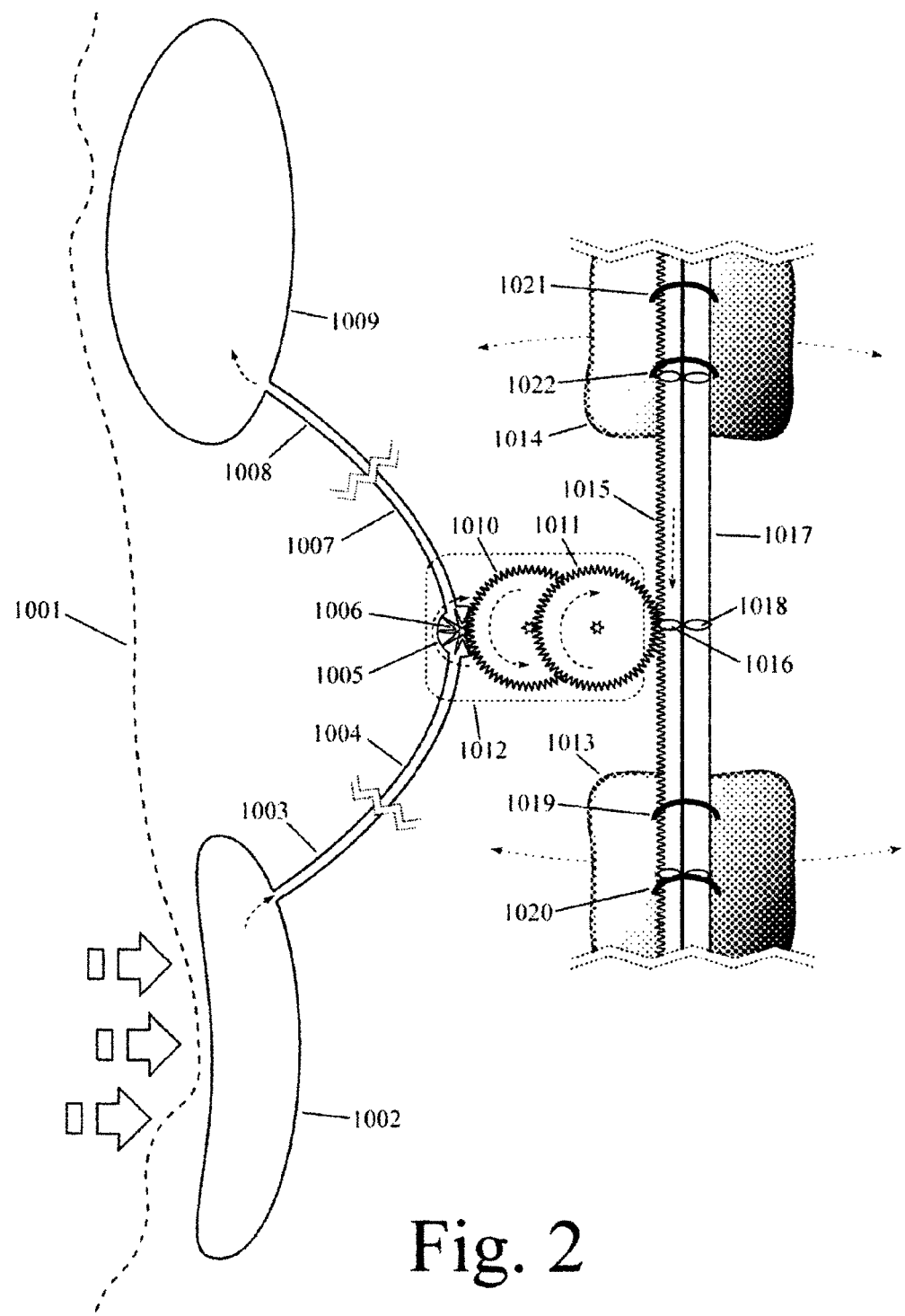

FIGS. 1 and 2 show one way to embody this device that transduces energy from the flow of a substance from an implanted reservoir in order to change the motion dynamics between a first member of the human skeletal system and a second member of the human skeletal system. FIG. 1 shows this embodiment when the substance is not yet flowing. FIG. 2 shows this embodiment after the substance has started to flow.

In further detail, the embodiment shown in FIG. 1 comprises: implanted reservoirs embodied as two saline-filled bladders 1002 and 1009; and a mechanism for transducing energy from the flow of the flowable substance into changes in the motion dynamics between two members of the skeletal system embodied as tube sections (1003, 1004, 1007, and 1008), circular chamber (1005), turbine (1006), gears (1010 and 1011), and parallel rods (1015 and 1017) that connect a first bone (1013) to a second bone (1014). The saline-filled bladders, connecting tubes, circular chamber, and rods are all shown in a cross-sectional side perspective in FIG. 1. A gear box 1012 that houses gears 1010 and 1011 is shown as if it were transparent (represented by a dashed outline) in order to more clearly show the gears inside.

In various examples, there may be one or more reservoirs that contain a flowable substance. These reservoirs are implanted into the human body. Movement of moving portions of the one or more reservoirs causes the flowable substance to flow. In various examples, there are energy-transducing mechanisms implanted into the human body that transduce energy from a flow of the flowable substance into changes in the motion dynamics between a first member of the human skeletal system and a second member of the human skeletal system. In various examples, one or more motion dynamics may be selected from the group consisting of: direction of motion; range of motion; and resistance to motion.

In the example shown in FIG. 1, the reservoirs are saline-filled bladders, 1002 and 1009, with flexible walls. These saline-filled bladders have been implanted within the body below skin layer 1001. In this example, these saline-filled bladders are sufficiently close to the skin layer that they can be compressed by moderate pressure from movement of a person's hand, or a chair, or some other object that is external to the body. In another example, these reservoirs may be implanted deeper into the body and they may be compressed, stretched, or otherwise moved by the relative movement of two or more internal members of the body. In this example, there are two implanted reservoirs. In other examples there may be only one reservoir or there may be more than two reservoirs.

In this example, the reservoirs containing a flowable substance are configured as bladders with flexible walls. In other examples, the reservoirs may be selected from the group consisting of: a sack; a bulb; a balloon; a disk; a tube; a hollow mesh; a layer with multiple bubbles or cells; and a chamber with telescoping or pleated walls. In various examples, the bladders and tubes may be made from material selected from the group consisting of latex, silicone, ethylene propylene diene monomer (EPDM), polyvinyl chloride, and polyurethane. In this example, the flowable substance in the reservoirs is a saline solution. In other examples, the flowable substance may be some (other) flowable substance such as some (other) liquid, gas, or gel.

In this example, there is a saline-filled tube, comprising tube sections 1003, 1004, 1007, and 1008, that connects the two bladders. Saline flows through this tube from bladder 1002 to the other bladder 1009 when bladder 1002 is compressed. In the figures that follow, we trace the flow of saline solution from bladder 1002 to bladder 1009. However, this device can also work with a flow from bladder 1009 to bladder 1002, depending on the desired change in the relative motion dynamics between members of the skeletal system. Even though the tube comprising sections 1003, 1004, 1007 and 1008 is a one continuous tube, we label it in different sections in order to more clearly reference different locations along the tube as we trace the flow of saline solution through the tube.

The zig-zag dashed lines between tube sections 1003 and 1004, and also between sections 1007 and 1008, are included in the figure in order to indicate: that the section of the tube in the zig-zag gap may be short or long, in different embodiments, and that optional components such as a wireless control unit may be inserted into the tube in this zig-zag gap. In this example, there is a relatively short distance of tube in zig-zag gap between tube sections 1003 and 1004. For example, the members of the skeletal system, 1013 and 1014 may be spinal vertebrae and the implanted saline-filled bladders may be just a couple inches away under the skin layer of the person's back. In this example, the bladders may be compressed by hand massage. In another example, there may be a relatively long distance of tube in the zig-zag gap. For example, the implanted saline-filled bladders may be some distance below the spinal area and compressed by sitting motion. In this example, there is no wireless control unit within the zig-zag gap. In another example, there may be a wireless control unit within the zig-zag gap. Many types of wireless control units are known in the prior art and the control unit is not central to the innovative features of invention. Thus, a specific type of wireless control unit is not specified in this description.

We now trace the path of the flow of saline solution from bladder 1002 to bladder 1009 that occurs when bladder 1002 is compressed. Saline solution leaves bladder 1002 and flows into tube section 1003. After flowing through the distance within the zig-zag gap, the flow enters tube section 1004. From tube section 1004, the flow then enters circular chamber 1005 that contains a paddle-wheel turbine 1006. The flow of saline solution through circular chamber 1005 rotates paddle-wheel turbine 1006.

The saline solution then exits the other side of circular chamber 1005, enters tube section 1007, goes through another zig-zag gap, enters tube section 1008, and finally enters into bladder 1009 which causes bladder 1009 to expand. This flow assumes compressive pressure on bladder 1002 and no pressure (or at least less pressure) on bladder 1009. In this example, the member that is rotated by the flow of saline solution through circular chamber 1005 is a paddle-wheel turbine 1006. In other examples, helical screws or other moveable members within circular chamber 1005 to transduce energy from the flow of fluid into rotational movement.

We now focus on what happens to the rotational energy that is created as the saline solution rotates paddle wheel turbine 1006. There are many ways in which the rotational energy from a turbine can be channeled into movement of one or more rods connecting two members of the skeletal system. In the example shown in FIG. 1, a series of gears is used for this purpose. In this example, there is a small gear in the middle of turbine 1006 whose teeth engage the outer teeth of gear 1010. In this gear sequence, there is also a small gear in the middle of gear 1010 whose teeth engage the outer teeth of gear 1011. Next, the outer teeth of gear 1011 engage ridges on one side of rod 1015. In this example, the gears are housed in gear box 1012. Gear box 1012 is shown as if it were transparent (represented by dashed lines) in order to more clearly show the gears inside it. This sequence of gears decreases the magnitude, and increases the power, of the rotational movement from turbine 1006 to linear movement of rod 1015. In other examples, there may be different gear configurations, or alternative non-gear mechanisms, for transducing the flow of the flowable substance into relative linear movement of one or more rods connecting members of the skeletal system.

We now focus on the configuration, structure, and movement of the rods that connect first bone 1013 to second bone 1014. In the example shown in FIG. 1, for the purposes of diagrammatic simplicity, there are only two parallel rods, 1015 and 1017, that connect bone 1013 to bone 1014. In this example, rods 1015 and 1017 are connected to bones 1013 and 1014 by braces 1019, 1020, 1021, 1022. In other examples, rods 1015 and 1017 may be connected to bones 1013 and 1014 by other connective hardware, such as pedicle screws. In various examples, the turbine, gears, rods, and connective hardware may be made from one or more materials selected from the group consisting of: alumina fiber, carbon fiber, cobalt alloy, Co—Cr alloy, epoxy resin, fluorine resin, magnesium alloy, methacrylic resin, polyether sulfone, polyethylene, polymethyl methacrylate, polypropylene, polystyrene, polytetrafluoroethylene, SiC fiber, silicon carbide, silicon nitride, silicone resin, stainless steel, titanium alloy, and unsaturated polyester resin. In an example, all of the components of the device may be selected to be non-responsive to magnetic fields so that patients with the implanted device may be safely imaged by a Magnetic Resonance Imaging (MRI) scanner.

In some respects, it is linguistically overreaching to refer to only two parallel rods as a "bundle" of rods. However, we use the term "bundle" when referring to only two rods in order to highlight the likelihood of other examples of this embodiment with a cluster or three, four, six, or more parallel rods to connect members of the human skeletal system. The optimal number of parallel rods (or other types of parallel longitudinal members) for connecting members of the skeletal system will likely depend on the empirical results of prototyping and clinical testing. Only two rods are shown in FIG. 1 for diagrammatic simplicity, but the general principles of rod configuration and changing alignment illustrated herein could be easily applied by someone skilled in the art to bundles of rods with three, four, six, or more parallel rods.

The bundle of rods provides a certain degree of resistance to movement between a first member of the skeletal system (bone 1013 in this example) and a second member of the skeletal system (bone 1014 in this example). In the configuration shown in FIG. 1, the bundle of rods allows relatively little movement between these two members. This relatively modest movement is represented in FIG. 1 by two sets of relatively short dashed-line arrows extending outwards from both sides of bone 1013 and from both sides of bone 1014. These dashed arrows indicate that the bundle of rods in this configuration allow modest lateral movement, and little or no longitudinal movement, of one bone relative to the other.

In this embodiment, rods 1015 and 1017 have areas and sections of greater and lesser flexibility along their lengths. For example, area 1016, indicated by an oval, is one of the areas of greater flexibility along the length of rod 1015. Area 1018 is one of the areas of greater flexibility along the length of rod 1017. In FIG. 1, rods 1015 and 1017 are longitudinally configured such that areas 1016 and 1018, with greater flexibility, are not aligned. In this non-aligned configuration, the overall bundle of rods is relatively less flexible and more resistant to relative movement between the bones that it connects. If the flexible areas were to be longitudinally aligned, then the overall bundle of rods would be relatively more flexible and less resistant to movement between the bones that it connects.

The overall degree (and, optionally the direction) of the flexibility of the bundle depends on the degree to which the areas of greater and lesser flexibility among the longitudinal members comprising the bundle are aligned. In this example, the areas of greater flexibility are oval components made with a material that is more flexible than the longitudinal sections of the rods between the ovals. In other examples, there may be a different type of bundle of substantially-parallel longitudinal members with areas of greater and lesser flexibility along their length. In some of these other examples, the longitudinal members may be rods with thicker and thinner areas along their length, or rods with joints or hinges at certain locations along their length, or segmented rigid members connected by a central wire or cord.

In various examples, the energy-transducing mechanism may include a bundle of substantially-parallel longitudinal members, each with areas of greater and lesser flexibility along their length (wherein the longitudinal members may be rods with thicker and thinner areas along their length, rods with joints at certain locations along their length, or segmented rods connected by a flexible wire or cord); wherein the overall degree and/or direction of flexibility of the bundle depends on the degree to which the areas of greater and lesser flexibility among the longitudinal members are aligned; wherein this bundle is configured to resist movement of the first member of the human skeletal system relative to the second member of the human skeletal system; and wherein energy from the flow of the flowable substance is transduced into changes in the alignment of the longitudinal members in the bundle.

FIG. 2 shows the same embodiment of the device that was shown in FIG. 1, but after compression of bladder 1002 from external pressure. In this embodiment, the flow of saline solution resulting from compression of bladder 1002 is transduced into changes in the alignment of the rods in the bundle of rods which, in turn, changes the bundle's resistance to relative movement between bones 1013 and 1014. Sequentially, in greater detail, pressure against the body from a hand or other object (represented in FIG. 2 by three arrows pressing against skin layer 1001) compresses saline-filled bladder 1002. This compression forces saline solution from bladder 1002 to flow into tube section 1003. It then flows through the gap structure and into tube section 1004. The saline solution then flows through circular chamber 1005 where it rotates turbine 1006. The flow of the saline solution then exits the other side of the circular chamber into tube section 1007, then into tube section 1008, and lastly into bladder 1009 which expands as a result.

In the embodiment shown in FIGS. 1 and 2, the reservoirs are flexible bladders whose walls may be moved. In this example, this force comes from pressure from a hand or other external object against the body. In another example, the reservoir walls may be rigid and there may be a moving member within the reservoir that causes the fluid inside the reservoir to move when the person moves in an accelerating or decelerating manner. In various examples the moving portions of a reservoir may be moved by means selected from the group consisting of: movement of an object external to the human body relative to the reservoir (such as pushing, pressing, pulling, compressing, squeezing, pumping, stretching, bending, twisting, shaking, or tilting movement); movement of the reservoir, and/or the human body within which it is implanted, relative to an object external to the human body (such as sitting, leaning or standing movement); movement of an internal member of the human body relative to the reservoir (such as extension, contraction, bending, or rotation movement); movement of the reservoir, and/or the human body within which it is implanted, relative to the force of gravity; and acceleration or deceleration of the reservoir and/or the human body within which it is implanted.

As shown in FIG. 2, the flow of saline solution causes clockwise rotation of turbine 1006, which in turn causes counter-clockwise rotation of gear 1010, which causes clockwise rotation of gear 1011, which causes downward movement of rod 1015 relative to rod 1017. In this example, this downward movement of rod 1015 relative to rod 1017 causes flexible area 1016 of rod 1015 to be longitudinally aligned with flexible area 1018 of rod 1017. This longitudinal alignment of flexible areas increases the overall flexibility of the bundle of rods (formed in this example by only two rods, 1015 and 1017) which allows a greater range of relative movement between bones 1013 and 1014. This greater range of allowable movement between bone 1013 and 1014 is represented in FIG. 2 by longer dashed arrows extending outwards from the sides of bones 1013 and 1014. In this manner, this device allows non-invasive adjustment of the motion dynamics allowed between bones.

In an example, there may be an optional control unit. This control unit may be wireless. In an example, this control unit may be inserted within the zig-zag gap between tube sections 1003 and 1004. In an example, this optional control unit may control the activation, degree, and/or direction of the transduction of energy from the flow of the flowable substance into changes in the motion dynamics of one member of the human skeletal system and a second member of the human skeletal system. In an example, this control unit may be outside, or operated remotely from outside, the human body. In an example, this control unit may respond automatically to information from sensors concerning the motion dynamics of members of the human skeletal system. In an example, this control unit may control valves that alter the flow of the flowable substance. Inclusion of an optional wireless control unit can provide a greater range of control. It also can offer a degree of automatic control based on information from sensors concerning the relative position and movement of members of the skeletal system. In an example, this control unit may be battery operated, but the power requirements for controlling the device (such as opening and closing valves) would still be much less than if electricity (rather than fluid flow) were the power source for actually moving the rods that connect the skeletal members.

The vision for this device, especially with the optional inclusion of a control unit and active response to sensor information, is that it could serve as a "smart device" for orthopedic adjustment. A "smart device" for orthopedic adjustment would enable adjustment of relative skeletal member motion dynamics for customization for different patients and even for different activities for the same patent at different times. The smart function is analogous, in some respects, to the manner in which smart pacemakers now adjust heart rates for different activities and the way in which insulin pumps adjust insulin levels for eating activities. It is likely that different degrees of spinal flexibility or rigidity are optimal for different activities such as playing sports, sitting and sleeping—but this has not been possible with technology in the prior art. The device disclosed herein can open up new opportunities for real-time orthopedic adjustment to provide the optimal level of flexibility or rigidity that matches each activity. This adjustment may be done manually, done automatically, or done by a combination of manual and automatic adjustments.

One application of this device is for dynamic stabilization of the spine. In an example, this device can change the motion dynamics between a first member of the human spine and a second member of the human spine. A primary goal of dynamic stabilization of the spine is to allow desirable motion of the spine with its natural range of motion, but to prevent injurious or painful motion outside its natural range of motion. It can be difficult to accomplish this selective movement with a single device due to variation in anatomy and physiology between patents and changes in load, anatomy, or physiology with age or with different activities for a given patent over time. The device described herein allows non-invasive adjustment of the relative position and movement of one member of the skeletal system relative to another member of the skeletal system. This allows customization for dynamic stabilization of the spine between patents and also allows adjustment of dynamic stabilization for a given patient over time with age or different activities.

Another application of this device is for long-term spinal distraction for correcting scoliosis or other spinal deformity. It is desirable to have a non-invasive way of gradually adjusting the direction and degree of spinal distraction to gradually correct spinal deformity without repeated invasive operations. The device described herein allows non-invasive gradual adjustments.

Another possible application of this device, especially when used in conjunction with an optional control unit and skeletal position sensors, is for prevention of back injuries. To be candid, this application is rather ambitious, but it could work and the potential payoff is very great if it does work. The harmful results of back injuries (including lost productivity, health care expenses, and hard-to-quantify but nonetheless significant chronic pain) are tremendous. A device that can both actively monitor and affect the relative position and movement of skeletal members could prove to be very useful for real-time detection and avoidance of potentially injurious movements.

Figure 3:
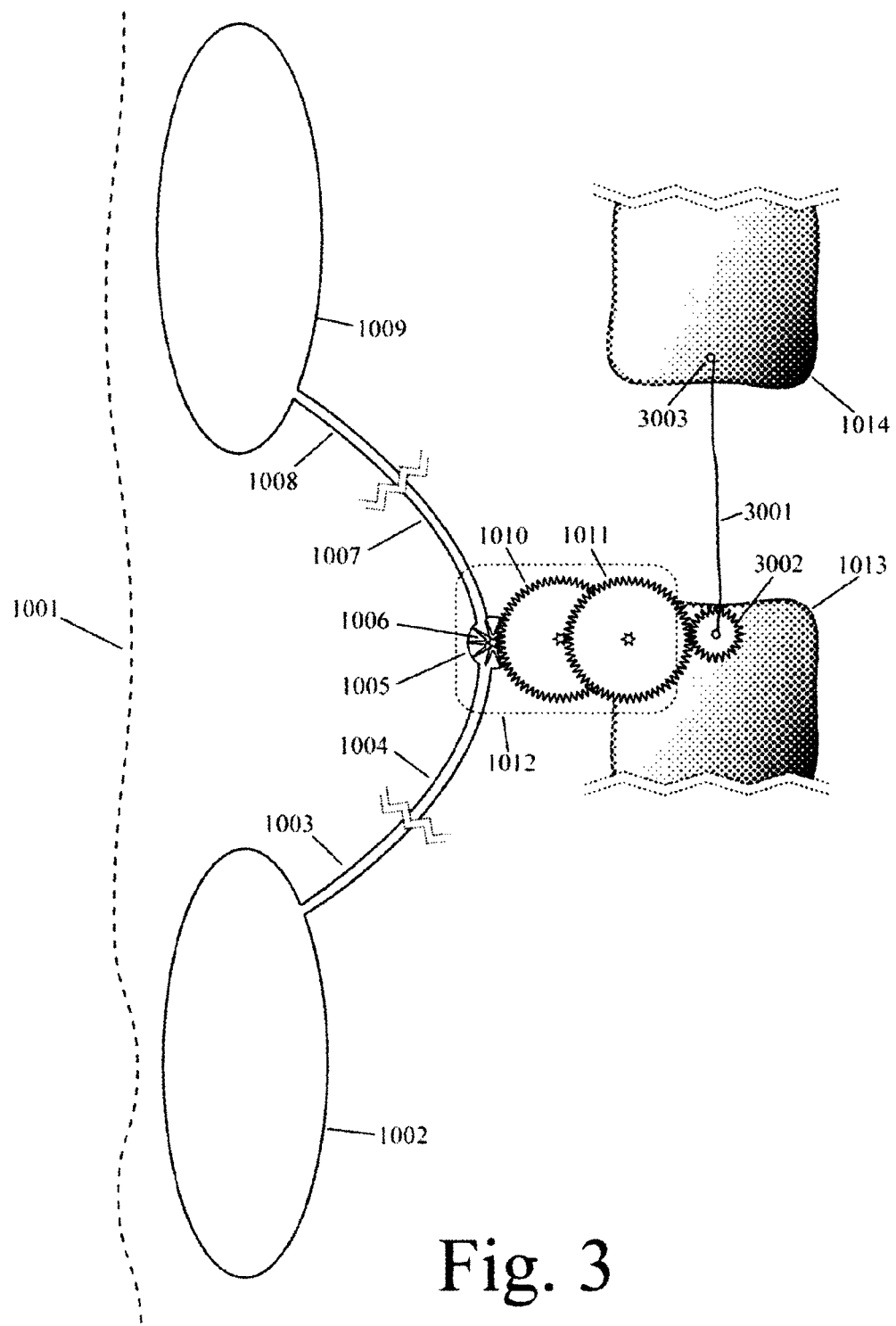
Figure 4:
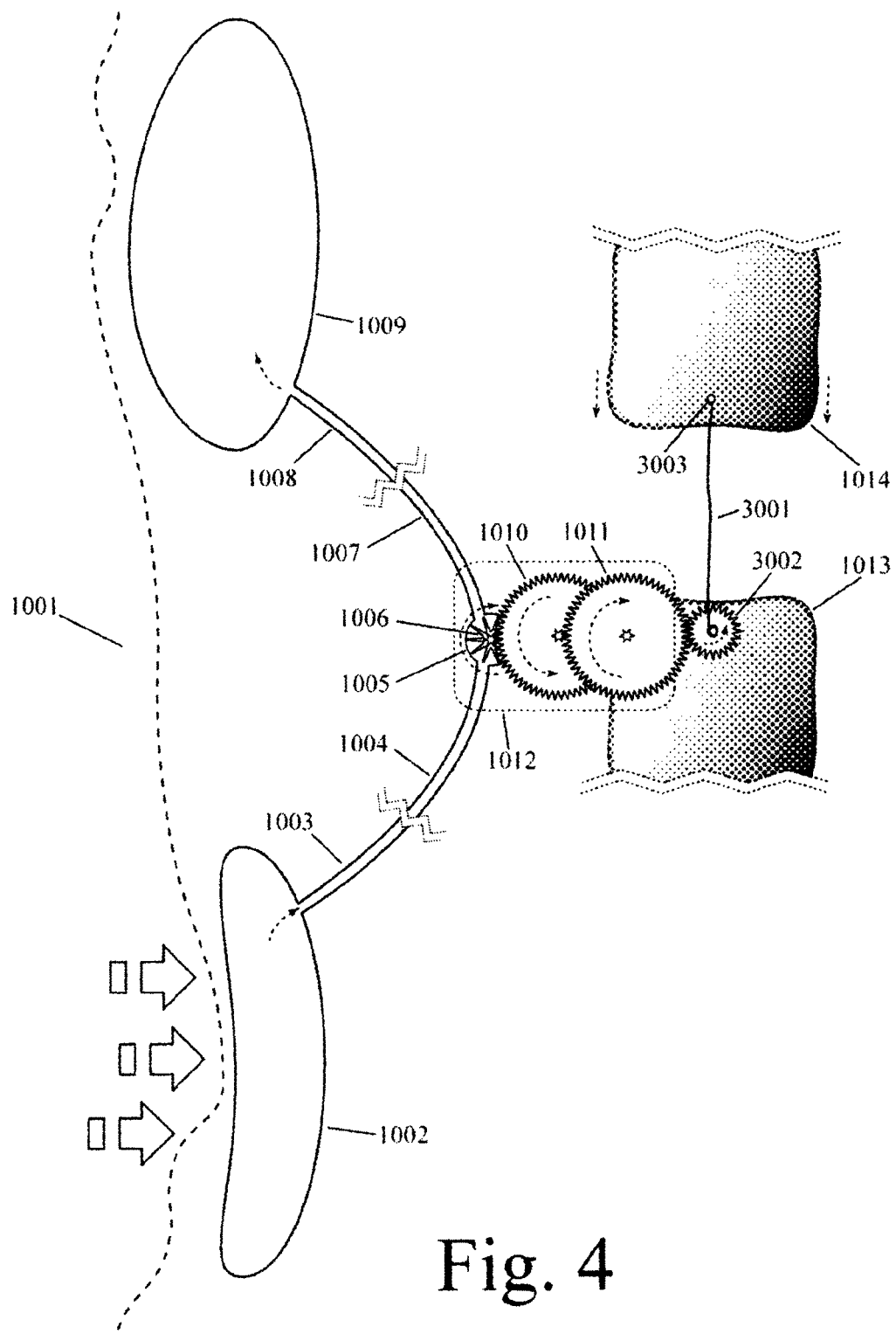

FIGS. 3 and 4 show another way to embody this device that uses the flow of a flowable substance to change the motion dynamics between a first member of the human skeletal system and a second member of the human skeletal system. FIG. 3 shows this new embodiment before a flow of the flowable substance. FIG. 4 shows this embodiment after a flow of the flowable substance.

In the embodiment shown in FIGS. 3 and 4, the energy-transducing mechanism includes one or more longitudinal flexible members (such as wires, filaments, cables, cords, chains, fibers, threads or bands), wherein these longitudinal flexible members are configured to create tension between the first member of the human skeletal system and the second member of the human skeletal system, and wherein energy from the flow of the flowable substance is transduced into changes in the length, tension, or length and tension, of the one or more longitudinal flexible members. Specifically, the embodiment in FIGS. 3 and 4 comprises: the same implanted reservoirs that were introduced in FIG. 1; and a mechanism for transducing a flow of the flowable substance into changes in the movement between two members of the skeletal system that is embodied as a sequence of components comprising turbine 1006, gears 1010 and 1011, spool 3002 and wire 3001 that connects bone 1013 and bone 1014. The perspective is similar to that of FIG. 1.

Since the bladders, tube sections, turbine, and first two gears of FIG. 3 are the same as those in FIG. 1, we will not repeat the description of them in this section. Instead, we will begin our discussion of the energy-transducing mechanism with spool 3002, which is the point at which this new embodiment diverges from the embodiment shown in FIGS. 1 and 2. Spool 3002 has outer teeth that engage the outer teeth of gear 1011. Accordingly, when the gear 1011 is rotated, it rotates spool 3002. One end of wire 3001 is attached to bone 1014 by screw 3003. The other end of wire 3001 is wound around the protruding central core of spool 3002. Thus, when gear 1011 is rotated, spool 3002 rotates and wire 3001 is wound (or unwound, depending on the direction of rotation) around spool 3002, which changes the tension and/or distance between bone 1014 and bone 1013. In some respects, this is analogous to the manner in which the tension of a guitar string is adjusted by rotating the tuning pegs around which one end of the wire is attached.

FIG. 4 shows the same embodiment that is shown in FIG. 3, but after compression of bladder 1002. In this example, compression of bladder 1002 causes a flow whose energy is transduced into increased tension, and decreased distance, between bone 1014 and bone 1013. In FIG. 4, the lower end of wire 3001 has been wound further around spool 3002, pulling bones 1014 and 1013 closer together. In this example, the longitudinal tensile connector between members of the skeletal system is a wire. In other examples, this longitudinal tensile connector may be a filament, cable, cord, chain, fiber, thread or band. In this example, there is only one connector. In other examples, there may be multiple tensile connectors. In other examples, these multiple tensile connectors may be housed within a longitudinal sheath or flexible tube. As was the case with the embodiment in FIGS. 1 and 2, a wireless control unit may be added to enable more precise manual, automatic, or combined manual and automatic control of the device. The ability to non-invasively adjust the tension and/or distance between members of the skeletal system can be useful for spinal distraction and correction of spinal deformities. It may also be useful, in conjunction with other structural connectors, for dynamic stabilization of the spine.

Figure 5:
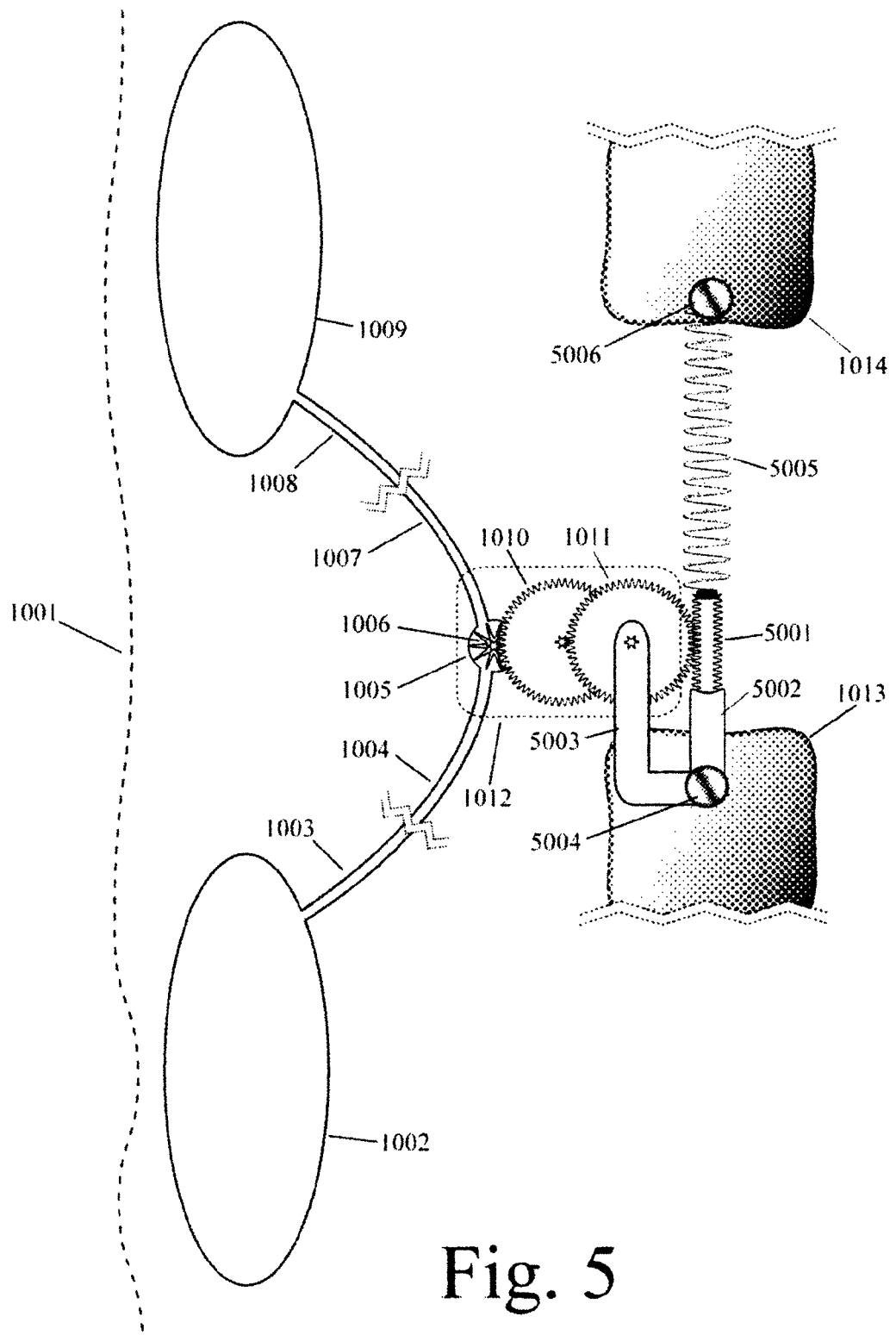
Figure 6:
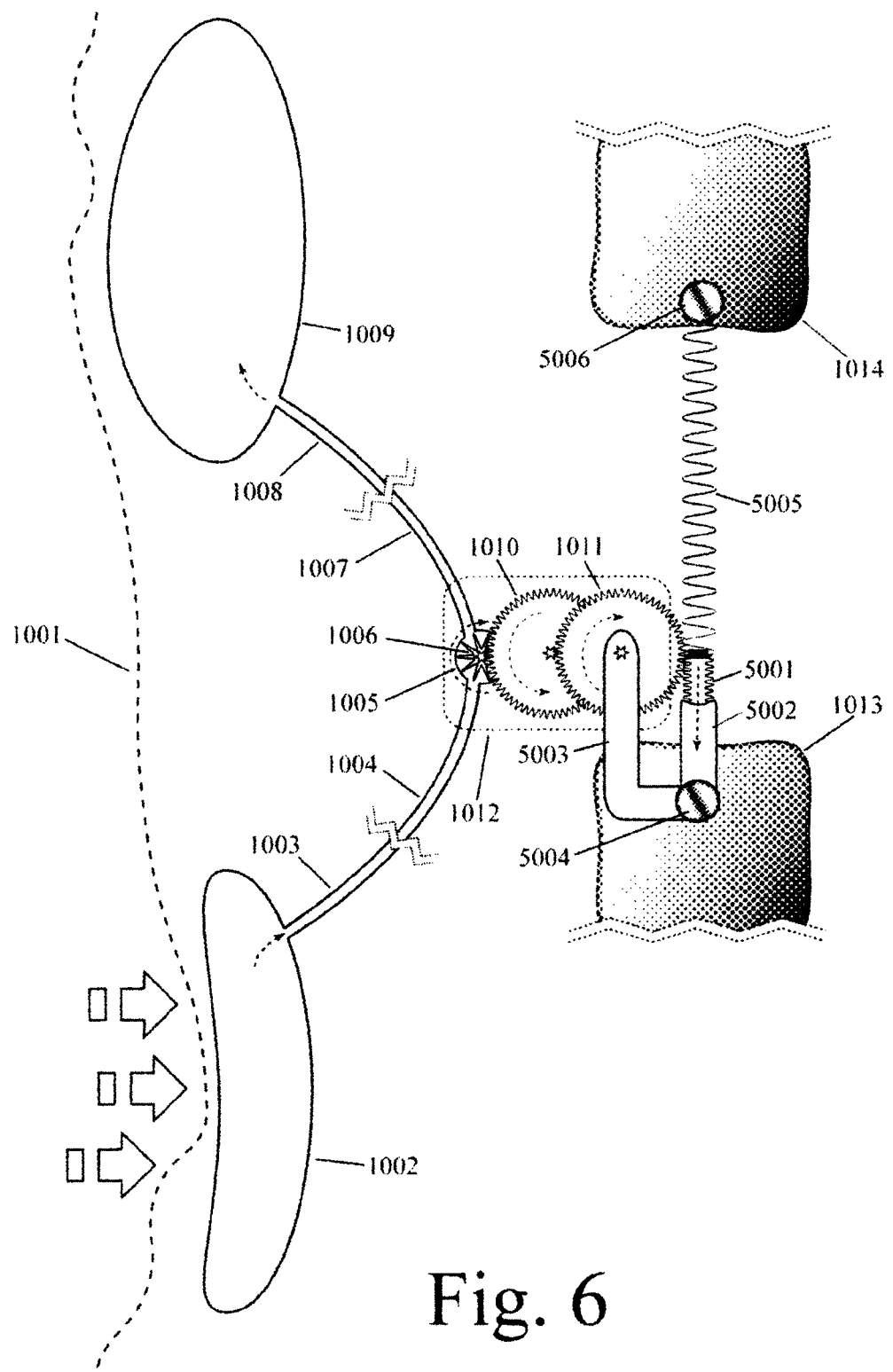

FIGS. 5 and 6 show another way to embody this device. In this embodiment, the energy-transducing mechanism includes one or more motion-dampening members (such as springs, rods with helical cuts, or elastic bands), wherein these motion-dampening flexible members are configured to dampen movement of the first member of the human skeletal system relative to the second member of the human skeletal system, and wherein energy from the flow of the flowable substance is transduced into changes in the length, tension, or length and tension, of the one or more motion-dampening members. Specifically, the embodiment in FIGS. 5 and 6 comprises: the reservoirs introduced in FIG. 1; and a mechanism for transducing a flow of the flowable substance comprising turbine 1006, gears 1010 and 1011, and notched rod 5001 and spring 5005 that span bone 1013 and bone 1014. Additionally, connectors 5003 and 5002 hold gear 1011 against notched rod 5001, screw 5004 attaches these connectors to bone 1013, and screw 5006 attaches spring 5005 to bone 1014.

Our discussion of the energy-transducing mechanism in this embodiment begins with notched rod 5001. This is the point in the energy-transducing sequence at which this embodiment diverges from that already described in FIG. 1. Clockwise rotation of gear 1011 moves notched rod 5001 downwards. In this example, downward movement of notched rod stretches spring 5005, which increases the tension between bones 1014 and 1013. In another example, depending on the interaction of the bones and the tensile force of the connecting spring, bones 1014 and 1013 may be drawn closer together. FIG. 6 shows the same embodiment shown in FIG. 5, but after compression of bladder 1002 resulting in extension of spring 5005. In this example, the motion-dampening member connecting the bones is a spring. In other examples, the motion-dampening member may be a rod with helical cuts or an elastic band. In this example, there is only one motion-dampening member. In other examples, there may be multiple motion-dampening members. As with previous embodiments, a wireless control unit may be added.

Figure 7:
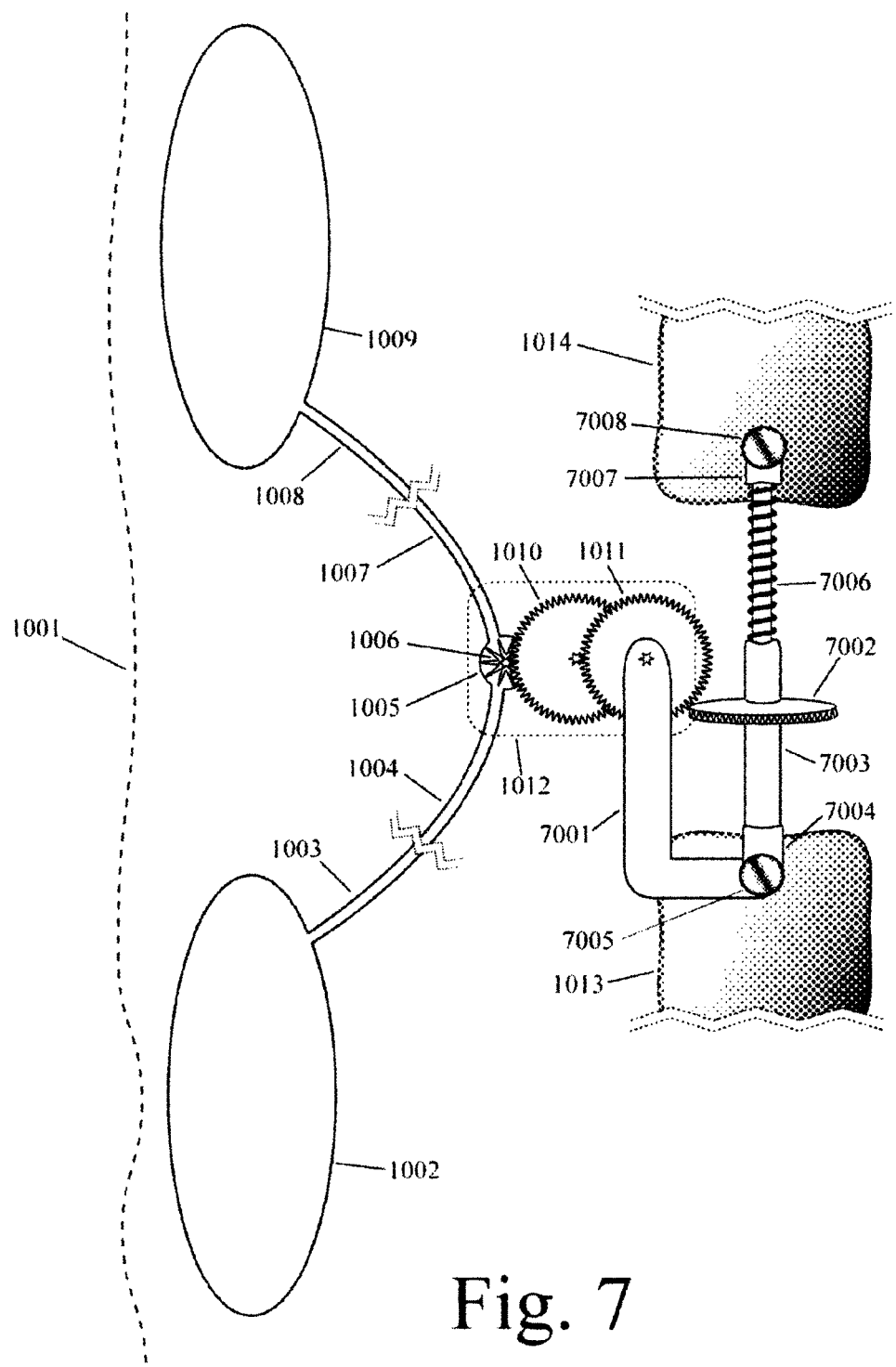
Figure 8:
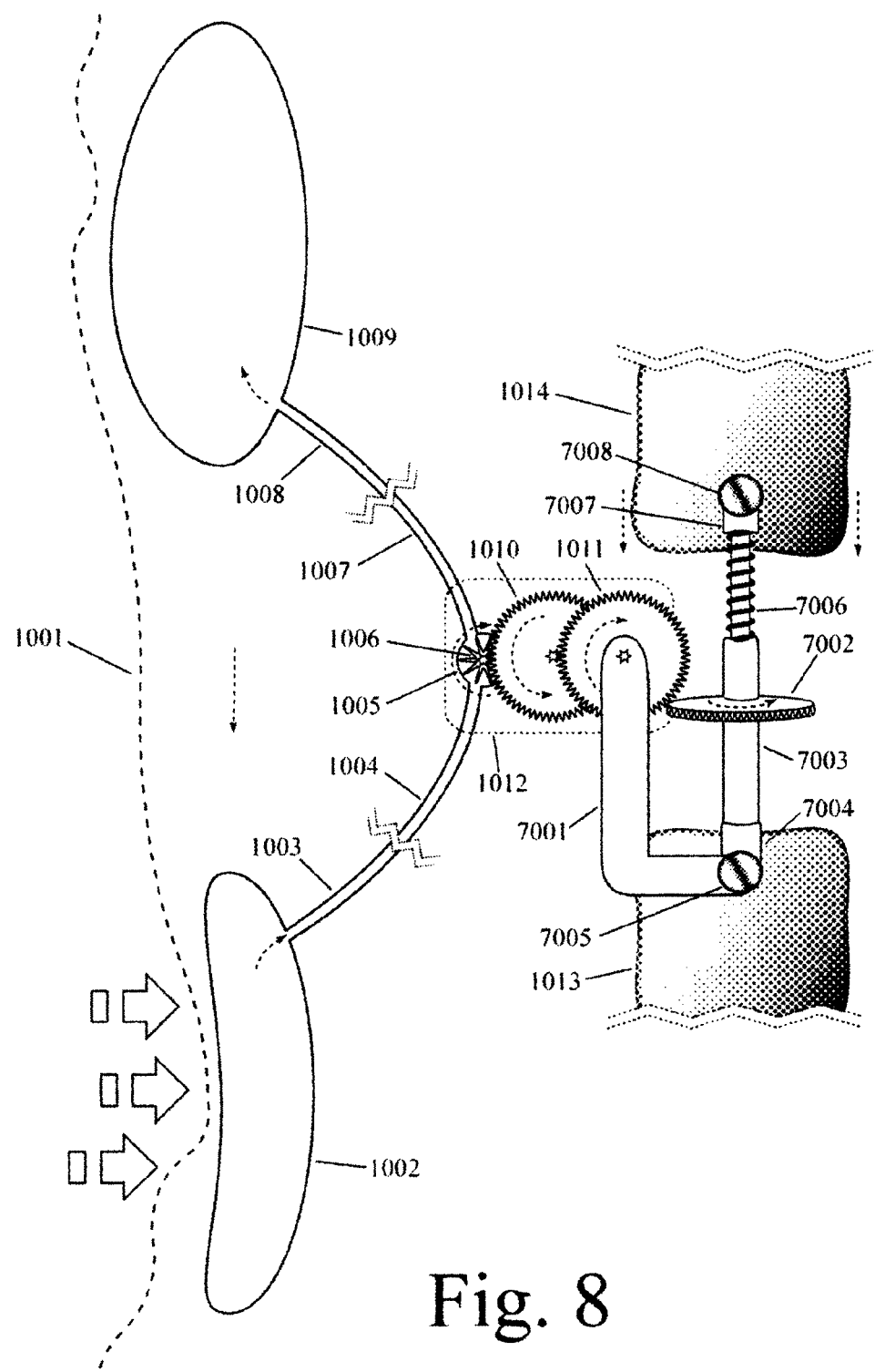

FIGS. 7 and 8 show another embodiment of this device. In this embodiment, the energy-transducing mechanism includes one or more pairs of thread-engaged members (such as a threaded rod within a correspondingly-threaded cylinder) wherein rotation of these members relative to each other extends or contracts their combined length, wherein these paired thread-engaged members are configured to constrain movement of the first member of the human skeletal system relative to the second member of the human skeletal system, and wherein energy from the flow of the flowable substance is transduced into rotation of the thread-engaged members relative to each other.

Specifically, the embodiment in FIGS. 7 and 8 comprises: the reservoirs introduced in FIG. 1; and an energy-transducing mechanism comprising turbine 1006, gears 1010 and 1011, bevel-toothed gear 7002, and threaded rod 7006. Additionally, connectors 7001, 7004, and 7003 hold gear 1011 against bevel-toothed gear 7002. Also, screw 7008 and connector 7007 attach threaded rod to bone 1014. Screw 7005 attaches connectors 7001 and 7004 to bone 1013. The teeth of gear 7002 are beveled and interact with the teeth of gear 1011 such that the planes of rotational movement for gears 1011 and 7002 are perpendicular to each other. Clockwise rotation of gear 1011 rotates gear 7002 counter-clockwise in a perpendicular plane. The counter-clockwise rotation of gear 7002, in turn, engages and pulls threaded rod 7006 downwards. This results in bones 1014 and 1013 being drawn closer together. FIG. 8 shows this embodiment after compression of bladder 1002, downward movement of threaded rod 7006, and bones 1014 and 1013 having been drawn closer together. As with previous embodiments, a wireless control unit may be added. This embodiment may be useful for dynamic stabilization of the spine or for spinal distraction.

Figure 9:
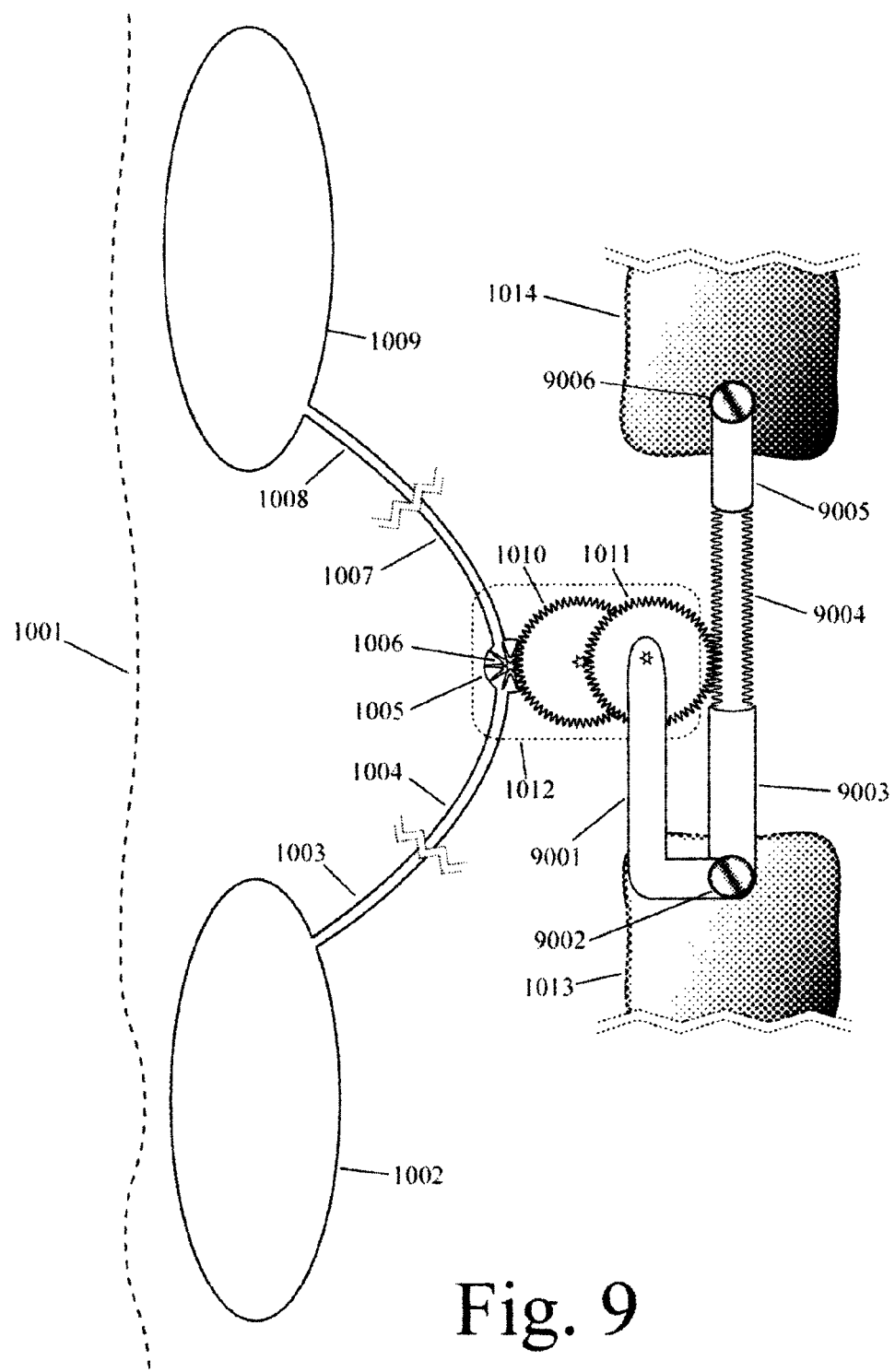
Figure 10:
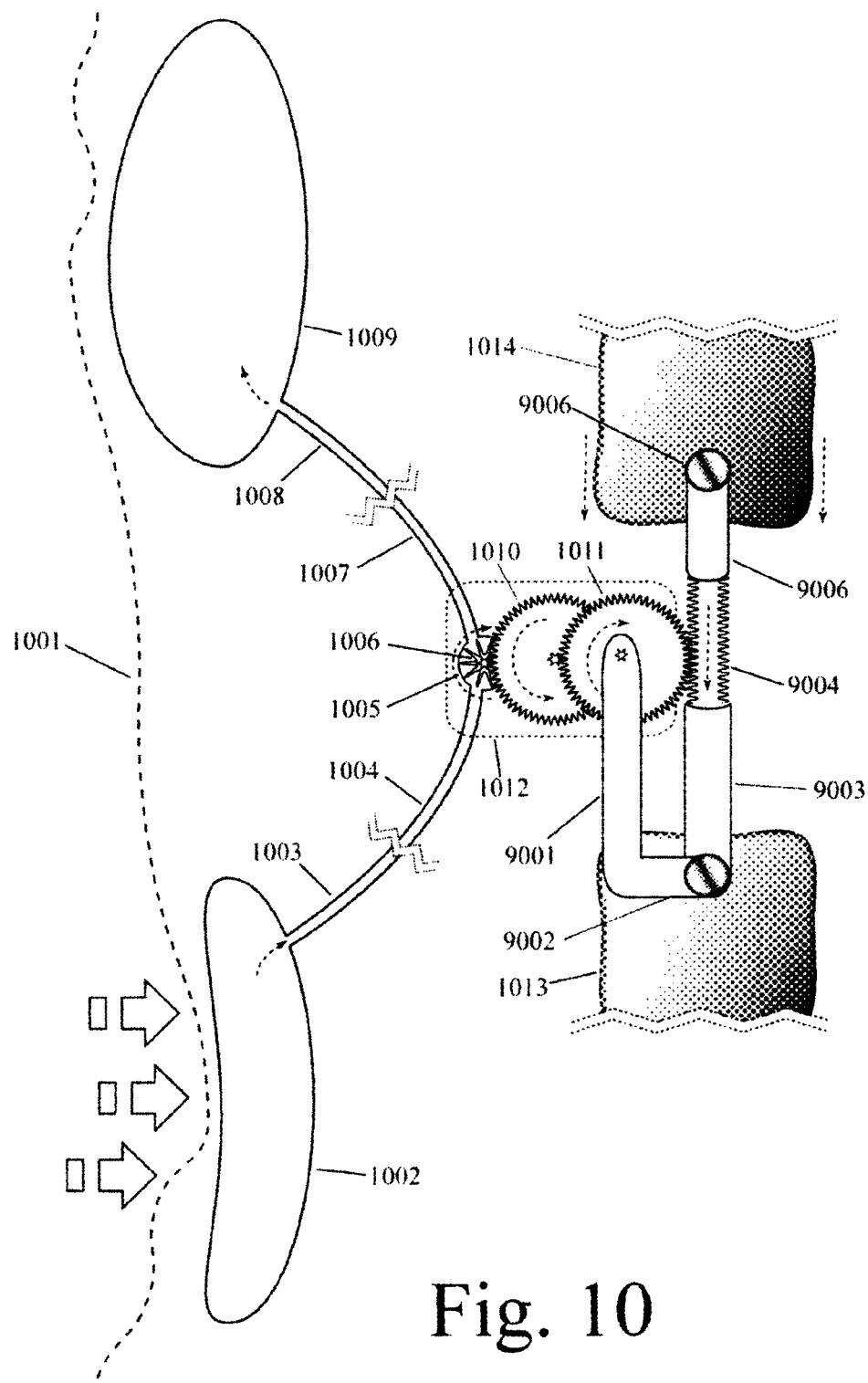

FIGS. 9 and 10 show an embodiment of this invention in which the energy-transducing mechanism includes one or more pairs of notch-engaged members (such as a notched rod engaged with a second member via a gear-tooth, ratchet, or escapement mechanism) wherein relative movement between the rod and the second member extends or contracts their combined length, wherein these paired notch-engaged members are configured to constrain movement of the first member of the human skeletal system relative to the second member of the human skeletal system, and wherein energy from the flow of the flowable substance is transduced into movement of the notch-engaged members relative to each other.

Specifically, the embodiment shown in FIGS. 9 and 10 comprises: the reservoirs introduced in FIG. 1; and an energy-transducing mechanism comprising turbine 1006, gears 1010 and 1011, and notched rod 9004. Additionally, connectors 9001 and 9003 hold gear 1011 against notched rod 9004, screw 9006 and connector 9005 attach notched rod to bone 1014, and screw 9002 attaches connectors 9001 and 9003 to bone 1013. Clockwise rotation of gear 1011 engages and pulls notched rod 9004 downwards. This results in bones 1014 and 1013 being drawn closer together. FIG. 8 shows this embodiment after compression of bladder 1002, downward movement notched rod 9004, and bones 1014 and 1013 having been drawn closer together. As with previous embodiments, a wireless control unit may be added. This embodiment may be useful for dynamic stabilization of the spine or for spinal distraction.

Figure 11:
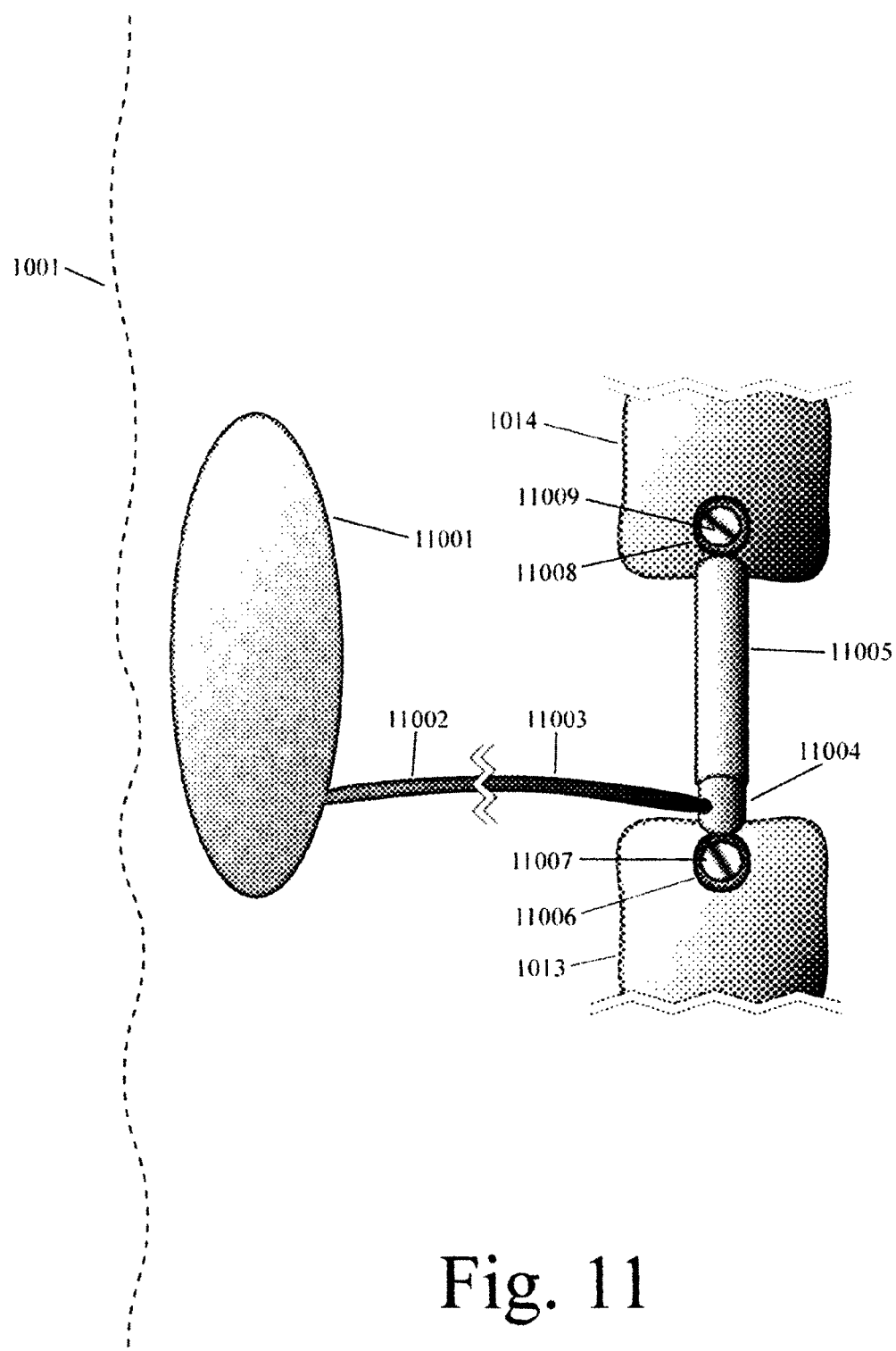
Figure 12:
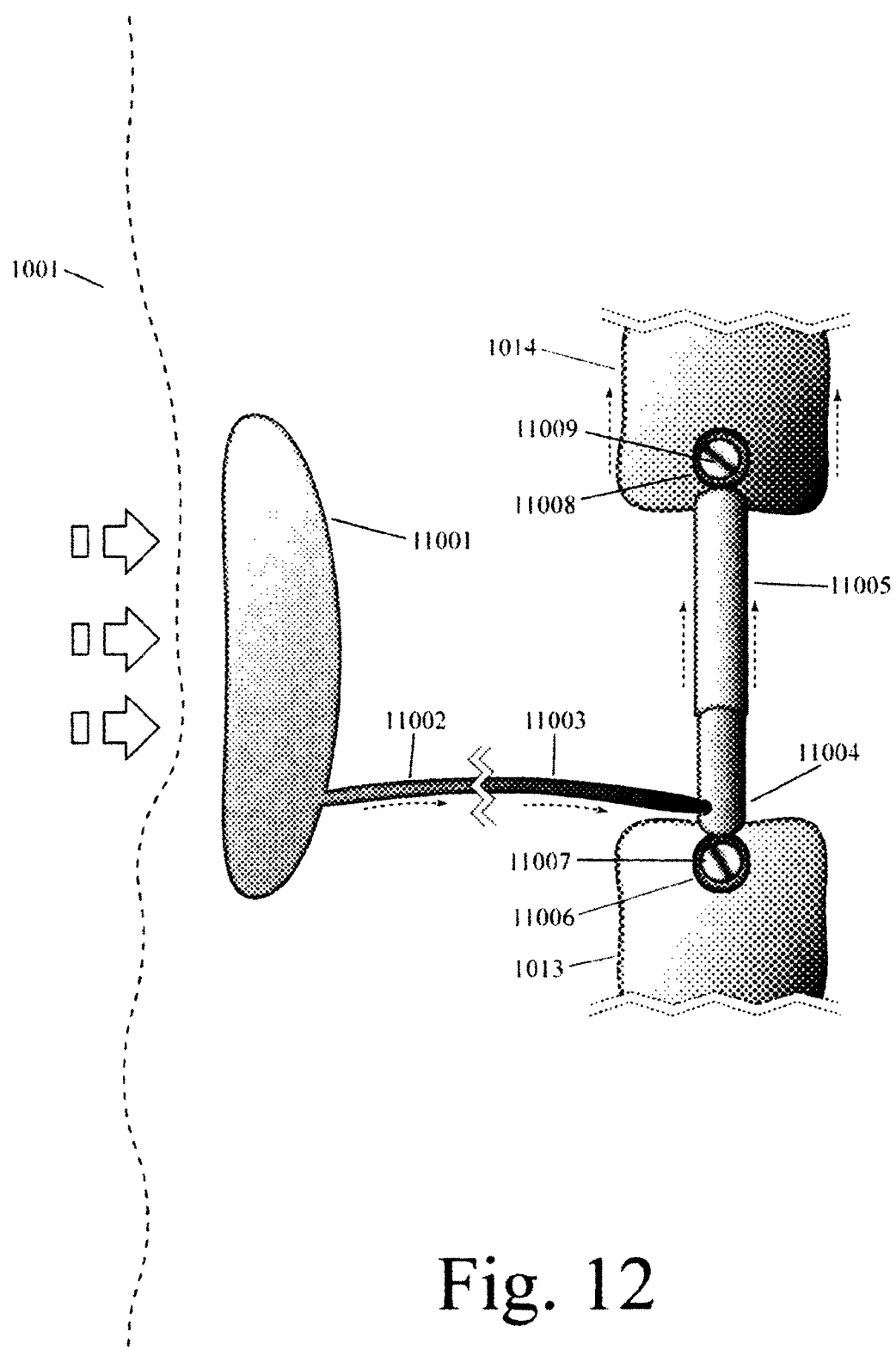

FIGS. 11 and 12 show an embodiment of this invention in which the energy-transducing mechanism includes one or more pairs of concentrically-overlapping members ("telescoping") filled with a flowable substance, wherein these one or more pairs of concentrically-overlapping members are configured to constrain movement of the first member of the human skeletal system relative to the second member of the human skeletal system, and wherein flow of the flowable substance changes the extension or contraction of these pairs of concentrically-overlapping members.

Specifically, the embodiment shown in FIGS. 11 and 12 comprises: a single saline-filled reservoir 11001 with flexible walls implanted below skin layer 1001; and an energy-transducing mechanism comprising tube sections 11002 and 11003 and concentrically-overlapping ("telescoping") members 11004 and 11005. Additionally, connector 11008 and screw 11009 attach member 11005 to bone 1014 and connector 11006 and screw 11007 attach member 11004 to bone 1013. Compression of reservoir 11001, as shown in FIG. 12, causes extension of concentrically-overlapping ("telescoping") members 11004 and 11005, which increases the distance between bones 1014 and 1013. A wireless control unit with controllable valves may be added in the zig-zag gap between tube sections 11002 and 11003. This embodiment may be useful for dynamic stabilization of the spine or for spinal distraction.

Figure 13:
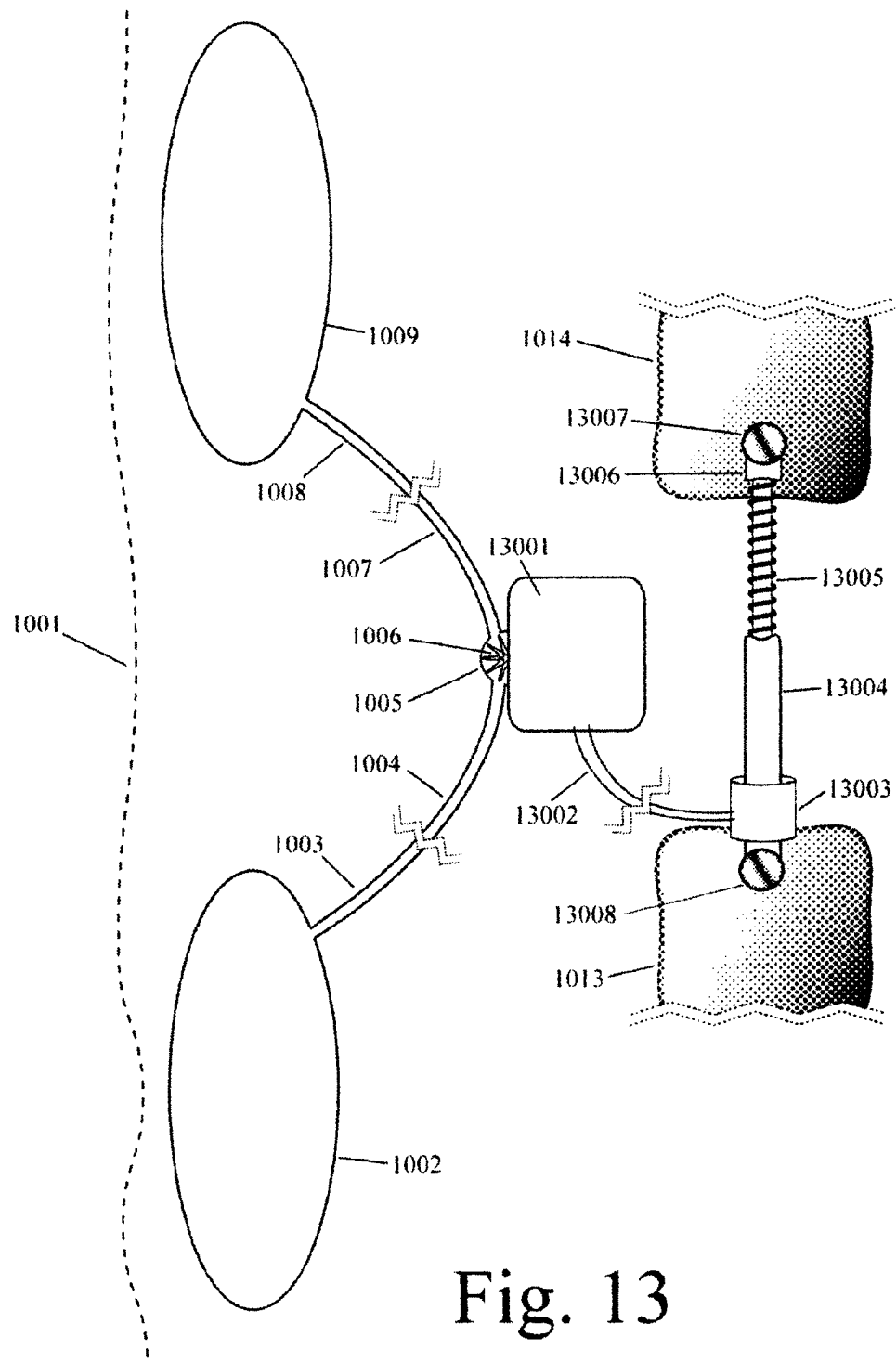
Figure 14:
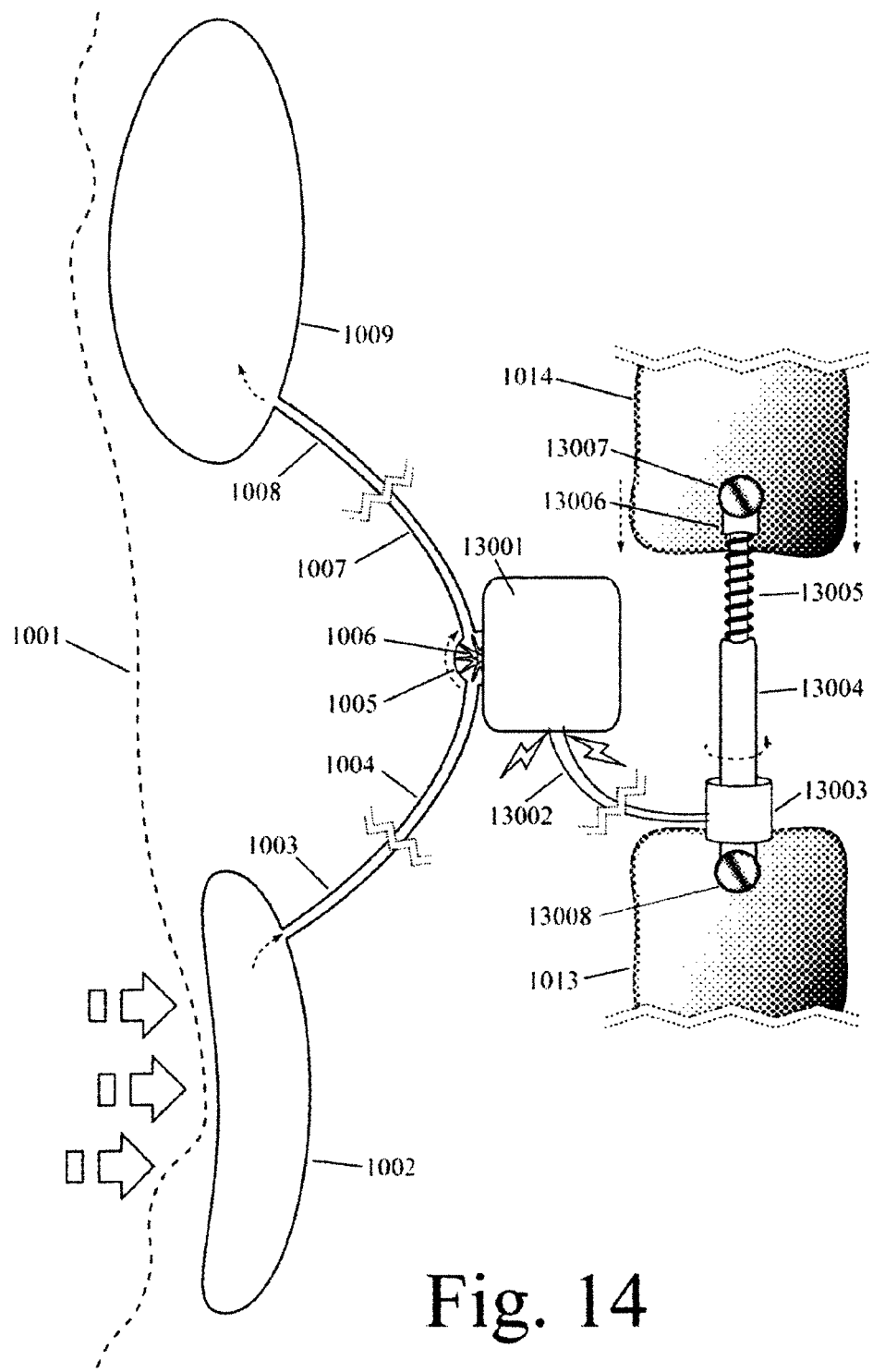

FIGS. 13 and 14 show another embodiment of this invention. In this embodiment the energy-transducing mechanism includes a member moved by an electric motor, wherein the moved member changes the motion dynamics of the first member of the human skeletal system relative to the second member of the human skeletal system, and wherein energy from the flow of the flowable substance drives (such as by movement of a turbine, propeller, impeller, wheel, blade, gear, or helical shaft) an electric generator that provides electricity to power the electric motor.

Specifically, the embodiment shown in FIGS. 13 and 14 comprises: the reservoirs first introduced in FIG. 1; and an energy-transducing mechanism comprising turbine 1006 that drives electric generator 13001, electric wires 13002 to electric motor 13003, and threaded rod 13005. Additionally, screw 13007 and connector 13006 attach threaded rod to bone 1014, threaded connector 13004 attaches threaded rod 13005 to electric motor 13003, and screw 13008 attaches electric motor to bone 1013. Compression of reservoir 1002, as shown in FIG. 14, causes the saline solution to flow, which rotates turbine 1006, which drives generator 13001, which powers electric motor 13003, which rotates threaded connector 13004, which pulls bones 1014 and 1013 closer together. In an example, a wireless control unit may be inserted into the zig-zag gap in wires 13002. In an example, a battery may also be added into the zig-zag gap in wires 13003 in order to store electricity from generator 13001. This embodiment may be useful for dynamic stabilization of the spine or for spinal distraction.

I claim:

1. A device to change the distance between a first member of the human skeletal system and a second member of the human skeletal system, comprising:
    a flowable substance, wherein this substance is a liquid, gas, or gel;
    reservoir, wherein this reservoir contains the flowable substance wherein this reservoir is configured to be implanted into the human body, and wherein movement of a moving portion of this reservoir causes the flowable substance to flow;
    a turbine, wherein this turbine is configured to be implanted into the human body, and wherein this turbine is rotated by a flow of the flowable substance;
    a pair of thread-engaged members, wherein this pair of thread-engaged members is configured to be implanted into the human body, wherein rotation of a first thread-engaged member relative to a second thread-engaged member changes the distance that these members span together, and wherein changes in the distance that these members span together change the distance between a first member of the human skeletal system and a second member of the human skeletal system; and
    a gear sequence that transduces rotation of the turbine into rotation of a first thread-engaged member relative to a second thread-engaged member, wherein this gear sequence decreases the magnitude of rotational movement when transducing rotational movement from the turbine to the first thread-engaged member.

2. The device in claim 1 wherein the reservoir is selected from the group consisting of: a bladder; a sack; a bulb; a balloon; a disk; a tube; a hollow mesh; a layer with multiple bubbles or cells; and a chamber with telescoping or pleated walls.

3. The device in claim 1 wherein the moving portions of the reservoir is moved by movement of an object external to the human body relative to the reservoir.

4. The device in claim 1 wherein the operation of the device is controlled by a control unit outside the human body, wherein this control unit controls the activation, degree, and/or direction of the transduction of energy from the flow of the flowable substance into changes in the distance between one member of the human skeletal system and a second member of the human skeletal system.

5. A device to change the distance between a first member of the human spine and a second member of the human spine, comprising:
- a flowable substance, wherein this substance is a liquid, gas, or gel;
- a reservoir, wherein this reservoir contains the flowable substance wherein this reservoir is configured to be implanted into the human body, and wherein movement of a moving portion of this reservoir causes the flowable substance to flow;
- a turbine, wherein this turbine is configured to be implanted into the human body, and wherein this turbine is rotated by a flow of the flowable substance;
- a pair of thread-engaged members, wherein this pair of thread-engaged members is configured to be implanted into the human body, wherein rotation of a first thread-engaged member relative to a second thread-engaged member changes the distance that these members span together, and wherein changes in the distance that these members span together change the distance between a first member of the human spine and a second member of the human spine; and
- a gear sequence that transduces rotation of the turbine into rotation of the first thread-engaged member relative to the second thread-engaged member, wherein this gear sequence decreases the magnitude of rotational movement when transducing rotational movement from the turbine to the first thread-engaged member.

6. The device in claim 5 wherein the operation of the device is controlled by a control unit outside the human body, wherein this control unit controls the activation, degree, and/or direction of the transduction of energy from the flow of the flowable substance into changes in the distance between one member of the human spine and a second member of the human spine.

* * * * *